United States Patent [19]

Yamada

[11] Patent Number: 4,751,927

[45] Date of Patent: Jun. 21, 1988

[54] HAIR IMPLANTATION METHOD AND DEVICE

[76] Inventor: Shiro Yamada, No. 2-7-1-606, Mita, Minatu-ku, Tokyo, Japan

[21] Appl. No.: 49,582

[22] Filed: May 13, 1987

[30] Foreign Application Priority Data

May 28, 1986 [JP] Japan .............................. 61-1211149

[51] Int. Cl.[4] .............................................. A61B 17/39
[52] U.S. Cl. .................................. 128/330; 128/800; 128/303.18
[58] Field of Search ................... 128/303.18, 330, 421, 128/422, 800

[56] References Cited

U.S. PATENT DOCUMENTS

| | | | |
|---|---|---|---|
| 1,059,631 | 4/1913 | Popovics | 128/330 |
| 3,062,214 | 11/1962 | Maxwell | 128/330 |
| 3,998,230 | 12/1976 | Miller | 128/330 |
| 4,221,212 | 9/1980 | Miller | 128/330 |
| 4,224,944 | 9/1980 | Roberts | 128/303.18 |
| 4,321,926 | 3/1982 | Roge | 128/303.18 |
| 4,378,019 | 3/1983 | Yamada | 128/330 |
| 4,550,728 | 11/1985 | Runyon et al. | 128/303.18 |

FOREIGN PATENT DOCUMENTS 1553950 10/1979 United Kingdom ............... 128/330

*Primary Examiner*—Dalton L. Truluck
*Assistant Examiner*—Frank Wilkens
*Attorney, Agent, or Firm*—Browdy and Neimark

[57] ABSTRACT

Apparatus and method for the implantation of artificial hair in human skin. The apparatus comprises a metallic hair implanting needle having an engaging part for engaging a hair root part of a strand of artificial hair at the tip end of the needle, and an external cylinder housing the hair implanting needle. A high frequency electric current generating device is provided in electric circuitry connection with the hair implanting needle, and a switch is provided for selectively supplying high frequency current from the generating device to the needle momentarily when the tip of the needle carrying the hair root part of artificial hair is inserted into the skin.

9 Claims, 2 Drawing Sheets

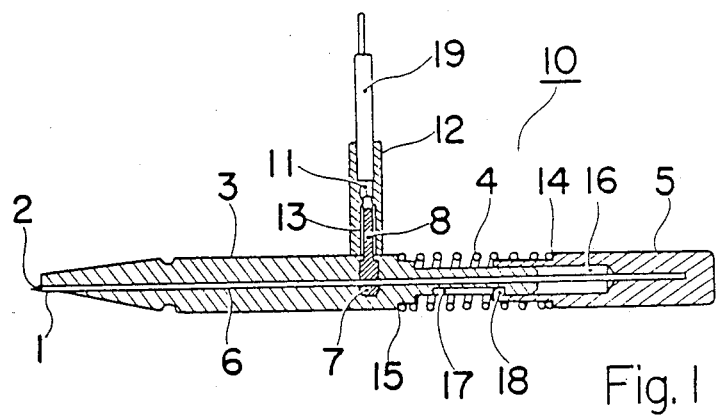
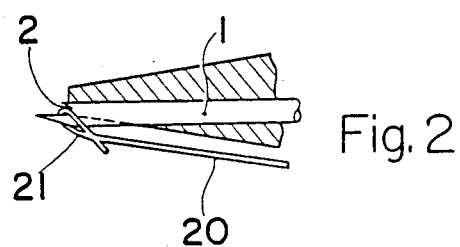
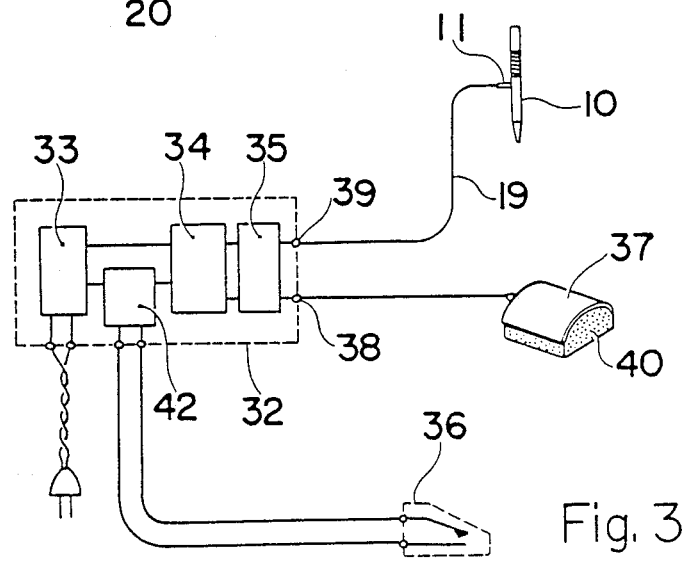

HAIR IMPLANTATION METHOD AND DEVICE

The present invention relates to improvements in devices for the implantation of artificial hair directly into human skin and to an improved method for this procedure.

More specially and in broad aspect, the present invention relates to a hair implantation device comprising a metallic hair implanting needle having an engaging part for engaging a hair root part of a strand of artificial hair at a tip end of the needle, and an external cylinder housing the hair implanting needle, and a high frequency electric current generating device in electric circuitry connection with the hair implanting needle, and a switch for selectively supplying high frequency current from the generating device to the needle momentarily when the needle carrying the hair root part of artificial hair is inserted into the skin.

Additionally in broad aspect the present invention relates to a method for implanting a strand of artificial hair into human skin comprising positioning a hair root part of a strand of artificial hair at a tip end of a metallic hair implanting needle, and inserting the tip end of the needle and the hair root part into the skin while simultaneously and momentarily passing high frequency electric current through the needle.

DISCUSSION OF PRIOR ART

Several proposals concerning improvement of hair implantation devices for loop shaped artificial hair directly to human skin have been proposed.

One of these proposals is described and claimed in Applicant's U.S. Pat. No. 4,378,019 which provides a hair implantation device wherein a tip end of a hair implanting needle which is freely slideable in an external cylinder is bifurcated and a looped hair root part engaged to the bifuracted part is pierced into skin during hair implantation. Although a relatively high success rate was realized by the device, yet the device was insufficient because of its still high falling rate of implanted hair within about one month after hair implantation. Usually, fibrous connecting tissue grows around an implanted hair pierced into subcutaneous tissue by the effect of a foreign matter, and implanted hair is first completely fixed when the hair root part is enclosed by the grown connecting tissue. About one month is usually necessary for the complete growth of the fibrous connecting tissue; while the growth of the fibrous connecting tissue is yet insufficient, the implanted hair is liably pulled off by a strong pulling force.

THE PRESENT INVENTION

An object of the present invention is to provide a hair implantation device and method capable of obtaining higher success rate in the stage of immediately after implantation of artificial hair by feeding high frequency current simultaneously with hair implantation coagulating subcutaneous tissue containing a looped hair root part by heating, and to prevent falling off of implanted hair while the growth of fibrous connecting tissue by the effect of a foreign matter is yet insufficient by giving at the same time with hair implantation a slight burn to the hair implanted part engaging the hair temporarily to the fibrous connecting tissue formed by the restoration of the burn in the course of about one week.

According to the present invention, a hair implantation device consists of a metallic hair implanting needle provided with an engaging part for a hair root part of artificial hair to a tip end of the needle and an external cylinder enclosing the foot of the needle, the present invention is characterized in order to achieve the above described object by connecting the above described hair implanting needle to a high frequency current generating device providing simultaneously a switch device for feeding high frequency current momentarily when the hair implanting needle is pierced into skin together with artificial hair, in a circuit connecting the hair implanting needle to a power source of the above described high frequency generating device.

BRIEF DESCRIPTION OF THE DRAWINGS

FIG. 1–FIG. 3 illustrate examples of the hair implantation device in accordance with the present invention.

FIG. 1 is a sectional view of the hair implantation device.

FIG. 2 is an enlarged figure of a part of a tip end of a hair implanting needle.

FIG. 3 is a drawing presenting a general concept of a high frequency generating device.

DESCRIPTION OF A PREFERRED EMBODIMENT

Figure 4:
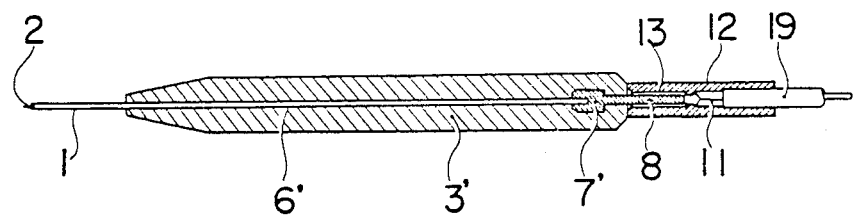
FIG. 4 is a sectional view illustrating another Example.

FIG. 1 and FIG. 2 illustrate an Example of a hair implantation device provided with a hair implanting needle fitted freely slidably to a hollow external cylinder. Namely, in FIG. 1, 1 is a hair implanting needle having a bifurcated tip end as illustrated by an enlarged figure (FIG. 2) constituting an engaging part 2 which engages a looped hair root part 1 of artificial hair 20. The foot of the hair implanting needle 1 is housed freely slidably in a central hole 6 of a hollow external cylinder 3 consisting of an insulating material such as plastic. A hind end of the hair implanting needle 1 is built-in in a cap 5 provided with a hollow groove 16 and fixed. The diameter of an external cylinder 3 of the cap 5 is reduced forming a step 14 for engaging a spring 4. Further, the diameter of the foot of the external cylinder 3 is also reduced forming a step 15 for engaging the spring 4, and the end of the external cylinder 3 is inserted freely slidably into a hollow groove 16 of the cap 5. Between the step 14 of the cap 5 and the step 15 of the external cylinder 3, there is a spring 4 having an impetus to move the both always in the opposite direction.

A metallic annular contact 7 is embedded in the middle part of the barrel of the external cylinder 3. The inside surface of the annular contact 7 is on the same level as the central hole 6 of the external cylinder 3. Therefore, the contact is exposed to the central hole 6 connecting electrically to the hair implanting needle 1 sliding in the central hole 6. Further, a projection is formed on the annular contact 7 constituting a terminal 8 exposing to the outside of the external cylinder 3.

The terminal 8 is connected to a cord 19 connected to a hereunder described high frequency generating device 32 by a connector 11 provided with a cylindrical spring contact 13 in a connector cover 12.

Further, a part of the side face of the foot of the external cylinder 3 is removed by engraving to form a sliding groove 17. On one hand, an end of a stopping pin 18 screw-fitted to the cap 18 reaches the sliding groove 17 preventing relative movement of the external cylinder 3 and the cap 5 in the revolutional direction, thus restricting the distance of protrusion of the hair implanting needle 1 when the cap 5 is pushed.

FIG. 3 illustrates a high frequency generating device 32 installed with a hair implantation device 10 in accordance with the present invention. The high frequency generating device 32 consists of a high frequency oscillator 33, an amplifier 34, and an output circuit 35, and the maximum output is usually 20 W; generated frequency is usually from 0.5 MHz to 10 MHz. Particularly, a foot switch 36 is provided in the circuit connecting the power source 43 to the hair implantation device 10, and a timer device 42 is also provided which feeds current for a certain time after closing the circuit by stepping the foot switch 36 and opening the circuit thereafter.

FIG. 4 illustrates another Example wherein a hair implanting needle is inserted into an external cylinder consisting of an insulating material and fixed thereto. The foot of the hair implanting needle 1 having a bifurcated engaging part 2 at the tip end is embedded in a central hole 6' of an external cylinder 3' consisting of an insulating material and fixed. A metallic contact 7' is built-in at the end of the external cylinder 3, which is connected to the hair implanting needle 1. A protrusion is provided to the contact 7' and the contact 7' is exposed to the outside of the external cylinder 3' constituting a terminal 8.

The terminal 8 is connected to a high frequency generating device 32 containing a foot switch 36 and a timer device 42 similarly to the device of the above described Example 1 by a connector 11 containing a cylindrical spring contact 13 in a connector cover 12.

Figure 5:
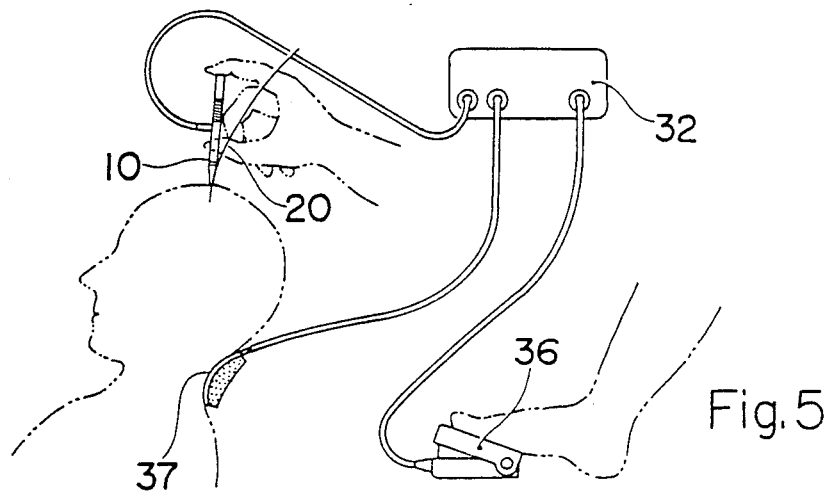
FIGS. 5 and 6 are drawings illustrating the state during use of the hair implantation device in accordance with the present invention.
Figure 6:
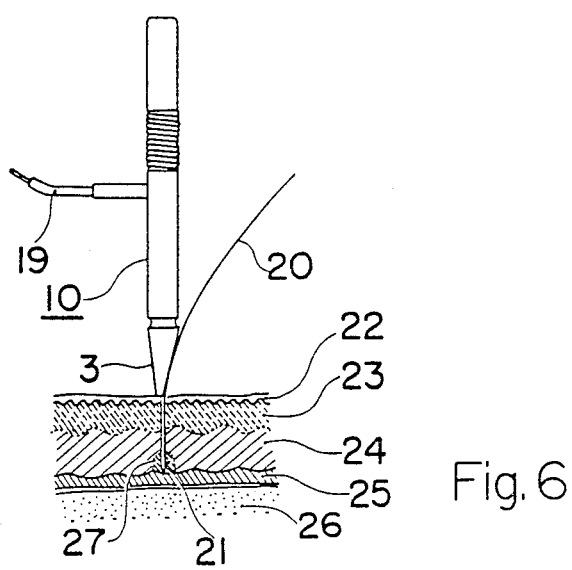

When the device is used, a counter electrode plate 37 connected to the terminal 38 of a high frequency generating device 32 provided also with cushioning sponge 40 bonded to the rear surface is, as illustrated by FIG. 5 and 6, laid under a head of a patient contacting with the skin of the patient, and the terminal 39 is connected to a connector 11 of the hair implantation device 10 through a cord 19. After engaging a hair root part 21 of artificial hair 20 to an engaging part 2 at the tip end of the hair implanting needle 1, the tip end of the hair implanting needle 1 is attached to the skin where hair is to be implanted, and the cap is pushed downward.

The hair implanting needle 1 slides through the external cylinder 3 and the tip end is pierced through the epidermis and corium deep into subcutaneous tissue 24. In this stage, the tip end of the hair implanting needle 1 is adjusted so as to reach just the surface of galea aponeurosis 25 consisting of firm fibrous tissue covering the surface of skull 26 by adjusting the position of the stopping pin 18.

When, in this stage, the circuit is closed by stepping the foot switch 36, momentary feed of high frequency current is generated to cause coagulation by heating 27 the subcutaneous tissue contacting with the tip end of the hair implanting needle 1 capturing thereby the looped hair root part 21 preventing thus falling of implanted hair root part.

If in this stage, a large current is fed, or a current feeding time is too long, the coagulation propagates to the surface of the skin. Accordingly, in order to cause selective coagulation of the part of the subcutaneous tissue only where the hair root part 21 is present, it is necessary to adjust the timer device 42 so as to feed the current for from 0.1 sec to 2 sec, preferably, for from 0.2 sec to 0.3 sec when a high frequency generating device having 20 W maximum output generating from 1 MHz to 2 MHz frequency is used.

When the wound is closed and the growth of fibrous connecting tissue begins around the looped hair root part 21 by the effect of burn immediately after hair implantation, the hair root part 21 is held by the subcutaneous tissue 12, so falling off of the implanted artificial hair will be prevented. If about one month is elapsed, the growth of the fibrous connecting tissue will progress further by the effect of a foreign matter, and the implanted hair root part 21 will be fixed firmly to the galea aponeurosis 25 by the combined effect with the fibrous connecting tissue formed by the burn. Thus, firm fixing of the artificial hair is accomplished.

As it may be apparent by the above-described explanation, falling of artificial hair immediately after hair implantation occurs hardly because only the part of the subcutaneous tissue contacting with the looped hair root part is coagulated by feeding high frequency current simultaneously with hair implantation by the device in accordance with the present invention, and the hair root part is held also by the fibrous connecting tissue generated by the burn. Moreover, since the coagulated part by the heating is so small as from 1 mm to 2 mm, the restoration of the injured tissue is quick, and the success rate is improved remarkably.

I claim:

1. A hair implantation device comprising a metallic hair implanting needle having an engaging part for engaging a hair root part of a strand of artificial hair at a tip end of the needle, and external cylinder housing the hair implanting needle, a high frequency electric current generating device, for generating an alternating electric current of 0.5 to 10 MHz, in electric circuitry connection with the hair implanting needle, and a switch for selectively supplying high frequency current of about 0.5 to 10 MHz from the generating device to the needle momentarily when the needle carrying the hair root part of artificial hair is inserted into the skin.

2. A device according to claim 1, wherein the switch is a foot activated switch.

3. A device according to claim 1, wherein the electric current generating device includes a timer to automatically control the length of time that the high frequency current is supplied to the needle, said time being about 0.1 to 0.3 second.

4. A device according to claim 1, wherein the electric circuitry of the generating device includes an electrode to be positioned in contact with an individual undergoing the implantation.

5. A device according to claim 2, wherein the electric circuitry of the generating device includes an electrode to be positioned in contact with the back of the neck of an individual undergoing implantation.

6. A device according to claim 3, wherein the electric circuitry of the generating device includes an electrode to be positioned in contact with the back of the neck of an individual undergoing implantation.

7. A method for implanting a strand of artificial hair into human skin comprising positioning a hair root part of a strand of artificial hair at a tip end of a metallic hair implanting needle;

and inserting the tip end of the needle and the hair root part into the skin so as to reach the top surface of the galea aponeurosis while simultaneously and momentarily passing high frequency alternating electric current of about 0.5 to 10 MHz through the needle.

8. Method according to claim 7, wherein the electric current has a 20 W maximum output and a frequency of from about 1 MHz to about 2 MHz and is supplied to the needle for a period of from about 0.1 to 0.3 seconds.

9. The method of claim 5, wherein a grounding electrode is positioned in contact with the back of the neck of an individual undergoing implantation.

* * * * *